(12) United States Patent
Corsi et al.

(10) Patent No.: US 9,726,678 B2
(45) Date of Patent: Aug. 8, 2017

(54) METHODS AND COMPOSITIONS FOR THE DIAGNOSIS AND PROGNOSIS OF ALZHEIMER'S DISEASE

(75) Inventors: Massimiliano Corsi, Milan (IT);
Stephen Peter Fitzgerald, Antrim (GB); John V. Lamont, Antrim (GB);
Paul Innocenzi, Antrim (GB)

(73) Assignee: RANDOX LABORATORIES LTD. (GB)

( * ) Notice: Subject to any disclaimer, the term of this patent is extended or adjusted under 35 U.S.C. 154(b) by 199 days.

(21) Appl. No.: 13/263,979

(22) PCT Filed: Apr. 15, 2010

(86) PCT No.: PCT/GB2010/050621
§ 371 (c)(1),
(2), (4) Date: Feb. 15, 2012

(87) PCT Pub. No.: WO2010/119286
PCT Pub. Date: Oct. 21, 2010

(65) Prior Publication Data
US 2012/0142548 A1 Jun. 7, 2012

(30) Foreign Application Priority Data

Apr. 15, 2009 (GB) .................................. 0906458.5

(51) Int. Cl.
| | |
|---|---|
| *G01N 33/53* | (2006.01) |
| *C40B 30/04* | (2006.01) |
| *C07K 16/00* | (2006.01) |
| *C12Q 1/00* | (2006.01) |
| *G01N 33/68* | (2006.01) |

(52) U.S. Cl.
CPC . *G01N 33/6896* (2013.01); *G01N 2800/2821* (2013.01)

(58) Field of Classification Search
None
See application file for complete search history.

(56) References Cited

U.S. PATENT DOCUMENTS

2011/0166166 A1* 7/2011 Henkin ................ G01N 33/543
514/263.34
2011/0229917 A1 9/2011 Krizman et al.

FOREIGN PATENT DOCUMENTS

| WO | WO-2006-134390 | 12/2006 |
|---|---|---|
| WO | WO-2011-067610 | 6/2011 |

OTHER PUBLICATIONS

Sevush et al. Platelet Activation in Alzheimer Disease. Apr. 1998. Arch Neurol, vol. 55, pp. 530-536.*
Mills et al. Vulnerable Caregivers of Patients with Alzheimer's Disease have a Deficit in Circulating CD62L-T Lymphocytes. Psychosomatic Medicine. 1998. vol. 61, pp. 168-174.*
Fenoglio et al. MCP-1 in Alzheimer's disease patients: A-2518G polymorphism and serum levels. 2004. Neurobiology of Aging. vol. 25, pp. 1169-1173.*
Zhao et al. Regulation of Membrane Metalloproteolytic Cleavage of L-Selectin (CD62L) by the EGF Domain. Published online May 24, 2001. J. Biol. Chem. pp. 1-37.*
Sokolova A et al., "Monocyte Chemoattractant Protein-1 Plays a Dominant Role in the Chronic Inflammation Observed in Alzheimer's Disease" *Brain Pathology*, 19:392-398.
Grammas P and Ovase R, "Inflammatory factors are elevated in brain microvessels in Alzheimer's disease" *Neurobiology of Aging*, 2001, 22:837-842.
Homeister JW et al., "Overlapping Functions of E- and P-Selectin in Neutrophil Recruitment During Acute Inflammation" *Blood*, 1998, 7:2345-2352.
Kozubski W et al., "Blood Platelet Membrane Fluidity and the Exposition of Membrane Protein Receptors in Alzheimer Disease (AD) Patients-Preliminary Study" 2002, 16(1):52-54.
Li, Y. et al. "ADAM17 deficiency by mature neutrophils has differential effects on L-selectin shedding" *Blood*, 2006, 108:2275-2279.
Babeluk, R. et al. "Implication of Wild Type Glutathione S-Transferase Omega-1 as a Risk Factor in Non-APOE4 Carriers in Alzheimer's Disease" *Clinical Chemistry*, 2009, vol. 55, No. 6, Supplement, pp. A223, Abstract E-42.
Cattabeni, F. et al. "Platelets Provide Human Tissue to Unravel Pathogenic Mechanisms of Alzheimer Disease" *Progress in Neuro-Psychopharmacology & Biological Psychiatry*, 2004, vol. 28, pp. 763-770.
Davies, T. et al. "Moderate and Advanced Alzheimer's Patients Exhibit Platelet Activation Differences" *Neurobiology of Aging*, 1997, vol. 18, No. 2, pp. 155-162.
Gupta, A. et al. "Coagulation and Inflammatory Markers in Alzheimer's and Vascular Dementia" *International Journal of Clinical Practice*, 2005, vol. 59, No. 1, pp. 52-57.
Li, Y-J. et al. "Revealing the Role of Glutathione S-Transferase Omega in Age-At-Onset of Alzheimer and Parkinson Diseases" *Neurobiology of Aging*, 2006, vol. 27, pp. 1087-1093.
Li, Y-J. et al. "Glutathione S--transferase omega-1 modifies age-at-onset of Alzheimer disease and Parkinson disease" Human Molecular Genetics, 2003, vol. 12, No. 24, pp. 3259-3267.
Marcourakis, T. et al. "Apolipoprotein E Genotype is Related to Nitric Oxide Production in Platelets" *Cell Biochemistry and Function*, 2008, vol. 26, pp. 852-858.

(Continued)

*Primary Examiner* — Channing S Mahatan
(74) *Attorney, Agent, or Firm* — Saliwanchik, Lloyd & Eisenschenk

(57) ABSTRACT

The invention relates to methods of diagnosing Alzheimer's disease (AD) in a subject and methods of determining the prognosis in patients with AD. The adhesion molecules P-selectin and L-selectin are described for the first time for use as biomarkers to aid in the diagnosis of AD. The invention further describes the use of one or more of L-selectin, MCP-1, IL-1α, IL-8 and IFN-γ to aid in the prognosis of either accelerated cognitive decline (ACD) or slow cognitive decline (SCD) in patients with AD.

14 Claims, 3 Drawing Sheets

(56) References Cited

OTHER PUBLICATIONS

Figure 1:
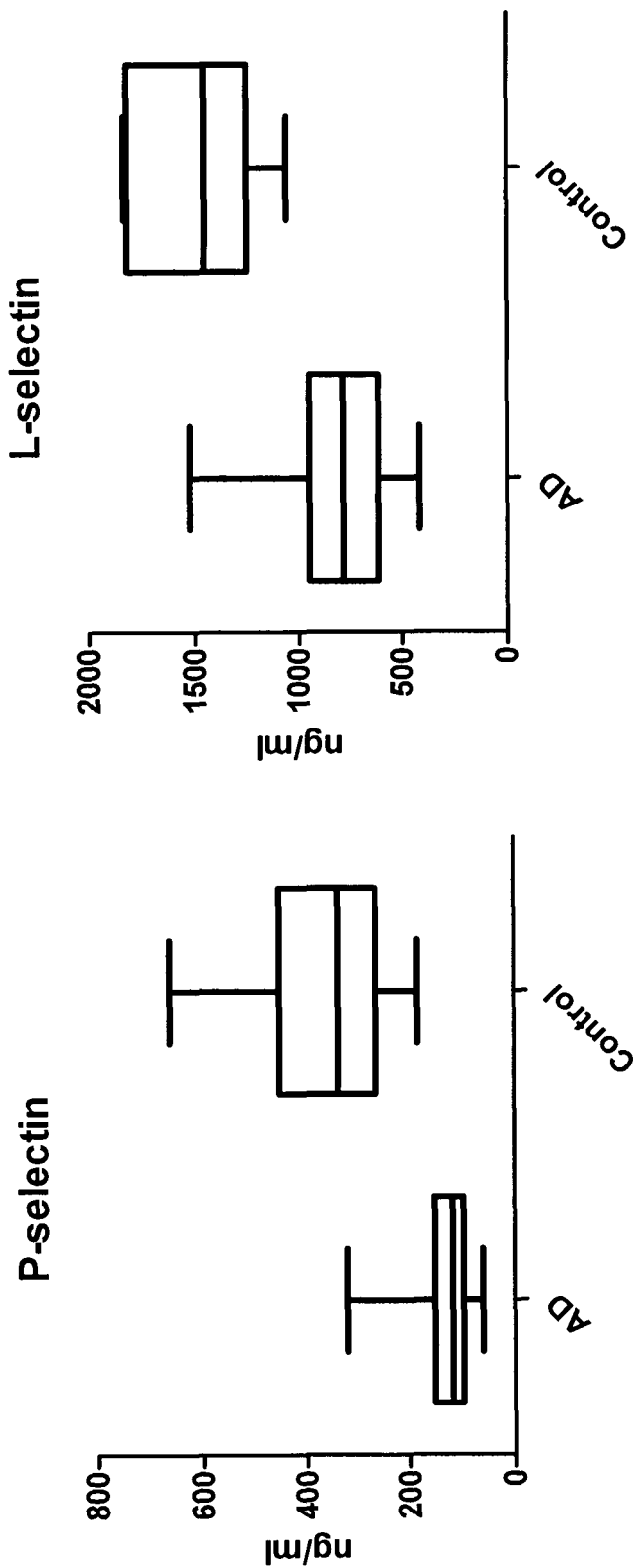

Matsushima, H. et al. "Reduction of Platelet Phospholipase C-Delta1 Activity in Alzheimer's Disease Associated with a Specific Apolipoprotein E Genotype (Epsilon3/Epsilon3)" *International Journal of Molecular Medicine*, 1998, vol. 1, pp. 91-93.
Smith, R. et al. "Platelet Monoamine Oxidase in Alzheimer's Disease" *Journal of Gerontology*, 1982, vol. 37, No. 5, pp. 572-574.
Zellner, M. et al. "Comparative Platelet Proteome Profiling from Alzheimer's and Parkinson's Disease Patients" *Clinical Chemistry*, 2009, vol. 55, No. 6, Supplement, pp. A221-A222, Abstract E-36.
Zhao, L. et al. "Macrophage-Mediated Degradation of Beta-Amyloid Via an Apolipoprotein E Isoform-Dependent Mechanism" *Journal of Neuroscience*, 2009, vol. 29, No. 11, pp. 3603-3612.

\* cited by examiner

METHODS AND COMPOSITIONS FOR THE DIAGNOSIS AND PROGNOSIS OF ALZHEIMER'S DISEASE

FIELD OF THE INVENTION

The present invention relates to biomarkers for Alzheimer's disease and in particular, methods of diagnosis of Alzheimer's disease using such biomarkers and kits for use in such diagnosis.

BACKGROUND OF THE INVENTION

Alzheimer's disease (AD) is a chronic neurodegenerative disease characterized by a progressive impairment of cognitive functions and memory loss. Neurofibrillary tangles, β-plaques, synapse loss and neuron loss are major pathologic hallmarks of the brain in individuals with AD. A role for chronic inflammation in the brain degeneration of AD sufferers has been suggested since the neurodegenerative processes are accompanied by reactive astrogliosis and microglia activation (Dickson et al.; Rogers et al.). Immunopathological studies have shown that amyloid plaques are associated with clusters of activated microglial cells expressing pro-inflammatory cytokines such as interleukin-1 (IL-1), interleukin-6 (IL-6) and other inflammation-related regulatory molecules. The immune system and the central nervous system (CNS) are complex tissues and few studies have attempted to investigate their interaction. The CNS has been labelled an immunologically privileged site and the presence of the blood brain barrier (BBB) reinforced the view that immunosurveillance is absent within the CNS. However, recent CNS investigations point to the localised production of molecules with an immune function and its accessibility to a small number of lymphocytes and monocytes (Akiyama et al.; Rebenko-Moll et al.). Mechanisms of microglia recruitment into normal brain under physiological conditions have not been established. In animal models, a limited number of mononuclear phagocytes are continuously recruited into the disease-free brain where they either differentiate into microglia or remain a distinct population; studies of the diseased brain suggest a similar mechanism, but the process is accelerated. In an AD mouse model, a specific chemokine receptor facilitated the recruitment of microglia from within the brain and monocytes from the blood surrounding (β-amyloid deposits. Disrupting this process accelerated the disease and the mice rapidly died. These results suggest that microglia accumulation result in increase (β-amyloid deposition, particularly in and around blood vessels. Previous studies on gene polymorphism association with AD reinforced the view that altered immune responses could play a role in pathogenesis of AD (Chiapelli et al.). Moreover, several cytokines such as IL-1α, IL-1β, IL-2, IL-8, Interferon-γ (INF-γ) and tumour necrosis factor-a (TNF-a) have been found to be associated with senile plaques, to be secreted by activated microglia, and to be implicated in the development of neuritic plaques. Other molecules such as monocyte chemotactic protein-1 (MCP-1), vascular endothelial growth factor (VEGF), epidermal growth factor (EGF), vascular cell adhesion molecule-1 (VCAM-1), intercellular adhesion molecule-1 (ICAM-1), E-selectin, P-selectin and L-selectin are involved in the trafficking of monocytes across the BBB.

Clinical diagnosis of AD often occurs long after the onset of the disease. It is usually first noticed by immediate family members who detect problems with short-term memory and unusual behaviour. Confirmation is achieved post-mortem by detecting the presence of the pathological hallmarks of the disease, amyloid β plaques and neurofibrillary tangles.

Current methodology to diagnose AD uses differential diagnosis which can involve patient interview and examination, details of patient's family and social history, blood testing to rule out other forms of dementia, psychological tests and neuroimaging. In addition, the presence of elevated levels of β-amyloid and tau proteins have been shown in many studies to be indicative of AD, but despite there being commercially available tests for these proteins, they are not yet clinically recognised for use in Alzheimer's diagnosis. The principal neuropsychological tests incorporate a memory test for diagnosing AD e.g. the Mini Mental State Examination (MMSE). Unfortunately, mild memory deterioration is commonly associated with ageing (as well as stress and depression) and often does not necessarily imply AD (Small et al.). Thus, there is great interest in both clinical and preclinical biomarkers.

Protein diagnostic biomarkers are an aid in the diagnosis of diseases. High specificity protein diagnostic markers of AD would provide an objective measure of disease progression and reduce costs. Such biomarkers are especially important for detecting the disease early (and discriminating AD from age-related mild memory deterioration) when therapeutic compounds have the greatest potential effect, but more importantly so that the patient and family can formulate a plan to manage the disease. Additionally, the identification of biomarkers of AD may further provide important insights into the pathogenesis of AD. To this end there have been several reports and patent applications reporting biomarkers of AD (e.g. WO 2005/052592, WO 2007/136614). However, the majority of these biomarkers have either yet to undergo full validation or have not been accepted/taken-up by the clinical community. Even if these biomarkers were to be validated and clinically utilised, there is always a need for additional biomarkers of AD with improved diagnostic and prognostic capabilities.

A prognostic test for gauging the rate of advancement of AD in patients with the disease is also clinically desirable.

Once diagnosed with AD, the average life-expectancy is from 8 to 12 years, although it can span from 3 to 20 years. The likely speed of AD progression is very much a factor of interest to the patient and patient's family, and facilitates a number of their decisions such as short and long-term care provision and participation in clinical drug trials. The progressive cognitive loss experienced by people with AD is often documented using the MMSE. This measurement provides information on the rate of change over time and aids in gauging the effectiveness of therapeutic interventions, measuring cognitive decline, and the planning of health care. However, this method has shortcomings: it requires several measurements to be taken over time, and as the patient's condition deteriorates, the procedure becomes more difficult to implement.

Doody et al. (2001) describe a method for estimating progression rates in AD using MMSE. The method requires three pieces of data: the expected MMSE value for a patient, the initial MMSE of the patient and a physician's estimate of the duration of AD in the patient. The problem of such a method is that it is resource intensive, requiring an initial MMSE test to be conducted and in-depth information to assess the duration of AD prior to the patient's presentation at the clinic. Other methods used to predict the rate of decline in AD patients have made use of expensive, specialist equipment such as magnetic resonance imaging and voxel-based morphometry. Therefore, there is also an urgent need for a rapid, supportive method that predicts whether AD patients are suffering from ACD or SCD.

There has been intensive research over the past decade to detect protein biomarkers of AD, principally in cerebrospinal fluid (CSF). Amyloid β protein and tau protein have been the subject of much research, and high levels of these proteins in CSF represent the most promising protein biomarkers of AD. However, these biomarkers have yet to receive total clinical acceptance, and the method has the added disadvantage of requiring a painful lumbar puncture procedure executed by a skilled physician, in order to obtain a CSF sample for analysis. More recently, there has been much interest in uncovering blood-derived protein biomarkers of AD (e.g. Hye et al., Zhang et al., WO 2005/052592).

The ideal biomarker would be one that is highly specific for a disease state. The complexity of the human body and its biochemical pathways, with many proteins being multifunctional and inter-dependent, suggests that such biomarkers, if existing, are likely to be rare. Furthermore, with one million proteins estimated to make-up the human proteome, it will be difficult to isolate and identify such rare proteins, and multi-biomarker combinations for disease identification are more likely. However, biomarkers with greater disease specificity, whether used alone or in combination with other biomarkers, are preferred. Regardless of the apparent specificity of an individual protein for a specific disease state, in practice its diagnostic or prognostic use is likely to be adjunctive, that is, as a support or aid to other proteins and methods in the diagnosis or prognosis of a disease.

SUMMARY OF THE INVENTION

Biomarkers for use in the diagnosis and prognosis of AD are discussed herein. Specifically, the present disclosure is based on the finding that certain proteins, not previously described as biomarkers of AD, are differentially expressed in peripheral biological fluids of patients suffering from AD and disease free patients. In certain embodiments, the proteins are P-selectin and L-selectin. Comparison and analysis of the levels of these proteins in a sample taken from a patient to a control, provides a method that aids in the diagnosis of AD.

In a first aspect, the present disclosure provides a method of diagnosis of Alzheimer's disease (AD) comprising:

measuring the concentration of at least one of P-selectin and L-selectin in an in vitro sample of a peripheral biological fluid of a person suspected of having AD, and comparing the concentration of the at least one of P-selectin and L-selectin in the in vitro sample to a control sample wherein a decrease in the concentration of at least one of P-selectin and L-selectin compared to the control is indicative of AD.

In a second aspect, the present disclosure provides a method of diagnosis of accelerated cognitive decline (ACD) or slow cognitive decline (SCD) in a patient with AD comprising:

measuring the concentration of at least one of L-selectin, MCP-1, IL-1α, IL-8 and IFN-γ in an in vitro sample of a peripheral biological fluid of a patient with Alzheimer's disease; and comparing the concentration at the least one of L-selectin, MCP-1, IL-1α, IL-8 and IFN-γ in the in vitro sample of a peripheral biological fluid to a control, wherein an increase in the concentration of the at least one of MCP-1, IL-1α, IL-8 and IFN-γ compared to the control is indicative of SCD and wherein a decrease in the concentration of L-selectin compared to the control is indicative of ACD.

In a third aspect, the present disclosure provides the use of at least one of L-selectin, MCP-1, IL-1α, IL-8 and IFN-γ as a biomarker in the diagnosis of ACD or SCD in a patient suffering from AD.

In a fourth aspect, the present disclosure provides the use of at least one of L-selectin, MCP-1, IL-1α, IL-8 and IFN-γ as a complementary biomarker in the diagnosis of ACD or SCD in a patient suffering from AD.

In a fifth aspect, the present disclosure provides the use of at least one of P-selectin and L-selectin as a biomarker in the diagnosis of AD.

In a sixth aspect, the present disclosure provides a kit for use in the diagnosis of Alzheimer's disease comprising at least one probe for P-selectin and/or L-selectin together with at least one probe for one or more known biomarkers of AD.

In a seventh aspect, the present in disclosure provides a kit for use in the diagnosis of Alzheimer's disease comprising at least one probe for P-selectin and/or L-selectin.

In a eighth aspect, the present disclosure provides a kit for use in the diagnosis of SCD or ACD in a patient suffering from AD comprising at least one probe for one or more biomarkers selected from L-selectin, MCP-1, IL-1α, IL-8 and IFN-γ.

DEFINITIONS

Biomarker

A characteristic of the human body, which in the case of the current disclosure is a biochemical, objectively measured and evaluated as an indicator of normal and pathogenic processes or of pharmacological responses to therapeutic intervention.

Complementary Biomarker

A biomarker that is used in conjunction with another biomarker, other biomarkers or other methods to increase the sensitivity and/or specificity of a test used in, for example, disease diagnosis and prognosis and drug efficacy testing.

Known or Proposed Biomarkers of AD

As proposed by the studies described within the Method Section, IFN-γ, IL-8, MCP-1 and VEGF have been described as potential biomarkers. Other known biomarkers are tau protein and β-amyloid proteins. The known and proposed biomarkers described herein are not an exhaustive list.

Control

The controls to be used for assessing whether there has been a change in the level of the diagnostic or prognostic biomarker can be the level of the diagnostic or prognostic biomarker:

in the patient prior to the onset of AD,
in suitable healthy patients,
from a suitable data set derived from literature values.

Accelerated Cognitive Decline (ACD)

For the purpose of the current disclosure, ACD in AD is defined by an AD patient whose MMSE score decreases by five or more points in a year.

Slow Cognitive Decline (SCD)

For the purpose of the current disclosure in AD is defined by an AD patient whose MMSE score decreases by less than 5 points in a year.

Peripheral Biological Fluids

These are mammalian fluids that are relatively readily accessible compared to cerebrospinal fluid. Examples are saliva, tears, sweat, urine, plasma and serum.

Probe

Any molecule capable of binding another molecule (the target molecule) for a sufficient time-span to enable the bound molecule to be detected. A multitude of probes together enable the quantification of the target molecule. In the current disclosure, the probe is preferably a monoclonal or polyclonal antibody and "individual" probes imply probes that are specific for the named analyte.

Figure 2:
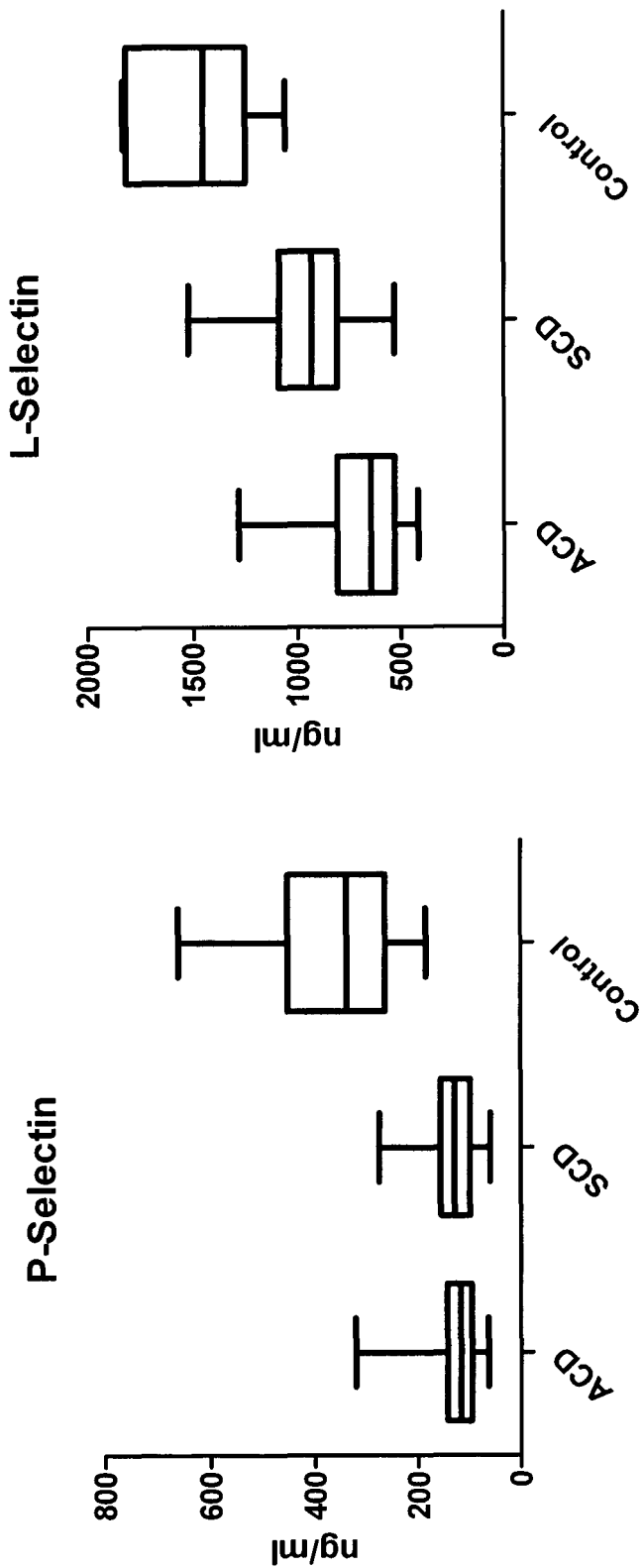
Figure 3:
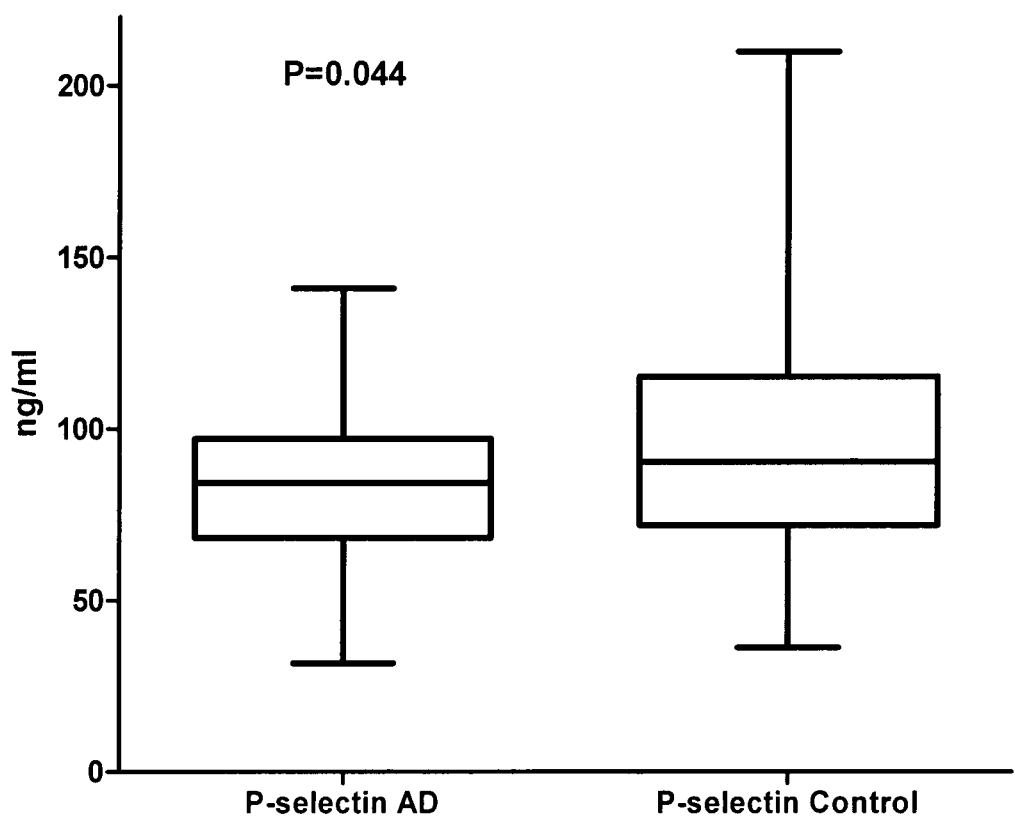

The compositions and methods disclosed herein are also described by way of examples with reference to the following Figures and Tables wherein:

FIG. 1 and Table 1 shows the median concentrations of P-selectin and L-selectin and other adhesion molecules and various cytokines in the plasma of AD patients compared to age-matched controls;

FIG. 2 and Table 2 shows the median concentrations (range in brackets) of P-selectin, L-selectin and other adhesion molecules and various cytokines in the plasma of AD patients with accelerated cognitive decline (ACD) or slow cognitive decline (SCD) compared to age-matched controls. Analyte concentration py/ml except for selections, ICAM-1 and VCAM-1 which are ng/ml. For a specific analyte, values with different letters are significantly different at the 5% level; and FIG. 3 shows the median concentrations of P-selectin in the plasma of AD patients compared to age-matched controls.

DETAILED DESCRIPTION OF THE INVENTION

The biomarkers disclosed herein can be detected or quantified alone. In certain embodiments, the biomarkers are may be detected or quantified in combinations of two or more P-selectin and/or L-selectin can be detected or quantified together with other biomarkers of AD, such as (but not limited to) MCP-1, IL-1α IL-1β, 1L-8, IFN-γ, MCP-1 and VEGF. Other biomarkers of AD with which the biomarkers disclosed herein can be combined to aid in diagnosis of AD include β-amyloid protein and tau protein. The peripheral biological fluid may be plasma or serum. Suitable controls can be, for example, the levels of biomarkers measured in the patient prior to the onset of AD, a disease-free patient group of a similar profile or a suitable data set derived from literature values. Differences in the relative amounts of the biomarkers between the AD patient and control aids in the prognosis of ACD or SCD. Recognized prognostic biomarkers for AD may be used in addition to the aforementioned proteins of the invention.

A further aspect of the disclosure is a kit for quantifying the amount of P-selectin and/or L-selectin alone or in combination with other biomarkers of AD, such as (but not limited to) MCP-1, IL-1α, IL-1β, IL-8, IFN-γ, MCP-1 and VEGF present in a peripheral biological fluid sample taken from a person suspected of having AD. In one embodiment, the kit comprises two sets of probe molecules for each of the target analytes. The first set of probe molecules may be immobilised onto a support surface while the second set of probe molecules may be mobile in the patient sample. In certain embodiments, the probe molecules are antibodies. The kit may be based on the sandwich ELISA format, comprising capture antibodies and detector antibodies for each of the proteins. The peripheral biological fluid can be plasma or serum. The kit optionally incorporates standards and controls. One or more recognised diagnostic biomarkers of AD may be used in conjunction with the aforementioned proteins of the invention.

Another aspect of the disclosure is a kit, which may be combined with or be separate from the diagnostic kit, for predicting or helping to predict whether an AD patient is suffering from ACD or SCD by measuring the amount of one or more of the proteins IL-8, IFN-γ, MCP-1, IL-1α and L-selectin in a peripheral biological fluid taken from the patient. In one embodiment, the kit comprises two sets of probe molecules for each of the target analytes. In one embodiment, the first set of probe molecules may be; immobilised onto a support surface while the second set of probe molecules may be in the patient sample. In certain such embodiments, the probe molecules are antibodies. The kit can be based on the sandwich ELISA format, comprising capture antibodies and detector antibodies for each of the proteins. The peripheral biological fluid may be plasma or serum. The kit optionally incorporates standards and controls. One or more recognized prognostic biomarkers for AD may be used in conjunction with the aforementioned proteins of the invention.

Certain embodiments of the disclosure are based on the finding that the adhesion molecule L-selectin is differentially expressed in the blood of patients suffering from ACD, SCD and controls. Furthermore, L-selectin and P-selectin are both expressed in decreased quantities in patients diagnosed with AD compared to controls. These findings enable L-selectin and P-selectin to be used in the prognosis of AD and as aids in the diagnosis of AD. The control could be a biological sample taken from: a healthy patient, the Alzheimer patient prior to the onset of AD, a suitable data set derived from literature values, or a patient afflicted with a disease other than AD for which the biomarker(s) used to diagnose AD is/are specific to AD. The expression level of the proteins is determined outside of the body of the person suspected of having the disease, using an in vitro assay. The proteins of the invention can be measured using the multi-analyte detecting immunodiagnostic platform, the Evidence Investigator, but any other suitable analytical platform may be used e.g. Western blot, ELISA, flow cytometry, 2D gel electrophoresis with mass-spectroscopy (2DGE-MS or 2DGE-MS/MS).

Also disclosed herein, is the discovery that the proteins P-selectin and L-selectin are differentially expressed in patients diagnosed with AD compared to patients without AD. Despite intense research into the detection of biomarkers for AD, no study has previously described either of L-selectin or P-selectin e.g. Abdi et al. (2006) identified more than 1,500 proteins in the CSF of Alzheimer's and disease-free patients; Hye et al. (2006) identified 211 proteins from the plasma of Alzheimer's patients; WO 2005/052592 list 250 proteins found in plasma or urine; WO 2007/1366614 describes 90 analytes in samples from Alzheimer's patients.

Furthermore, few reports describe the reduction of P-selectin levels in the blood of diseased patients compared to disease-free patients (Magro et al. 2004; Koutrobakis et al. 2004). These studies relate to Crohn's disease and systemic arterial disease, the latter study contradicting numerous studies which show P-selectin levels rising in such a condition. This makes P-selectin a highly specific biomarker for use in supporting the diagnosis of AD.

Certain embodiments of the disclosure make use of P-selectin and L-selectin either individually or in combination as an aid in the in vitro diagnosis of AD in a 10 patient, and as a complementary biomarker or complementary biomarkers, to aid the in vitro diagnosis of AD in a patient.

A further aspect of disclosure is the use of P-selectin and/or L-selectin and one or more of IL-1α, 1L-1β, IL-8, IFN-γ, MCP-1 and VEGF as an aid in the in vitro diagnosis of AD in a patient.

The disclosure further describes the use of one or more of L-selectin, MCP-1, IL-1α IL-8 and IFN-γ in the prognosis of AD or as complementary biomarkers to aid in the in vitro prognosis of AD.

A further embodiment is the use of L-selectin in the in vitro prognosis of AD. Another embodiment of the disclosure is a method that aids in the diagnosis of AD comprising measuring the concentration of P-selectin and/or L-selectin alone or in conjunction with one or more known biomarkers of Alzheimer's disease in a peripheral biological fluid taken from a person suspected of having Alzheimer's disease, and determining whether the concentration of two or more of these proteins is different compared to a control. The known biomarkers can be IL-1α, IL-1β, IL-8, IFN-γ, MCP-1 or VEGF. The known biomarkers can also be, for example, tau protein and/or β-amyloid proteins.

A further embodiment of the disclosure is a method for diagnosis of ACD and SCD in a patient suffering from AD. Such a method may be used in the prognosis or as an aid in the prognosis of AD. The method comprises measuring the concentration of one or more of L-selectin, MCP-1, IL-1α, IL-8 and IFN-γ in a peripheral biological fluid, and determining whether the concentration of one or more of said biomarkers is altered compared to a suitable control, said alteration indicating that the person has either accelerated cognitive decline of slow cognitive decline. These biomarkers may be used in conjunction with other known prognostic biomarkers.

In one embodiment, the following altered protein concentrations in peripheral biological fluids compared to controls are used to aid in the diagnosis of AD:
  a decrease in the level of P-selectin and/or
  a decrease in the level of L-selectin
  and
  an increase in the level of one or more of IL-1α, IL-1β, IL-8, IFN-γ, MCP-1 and VEGF.

In another embodiment, one or more of the following altered protein concentrations in peripheral biological fluids compared to controls are used in the prognosis or as an aid in the prognosis of a patient with AD:
  a decrease in the level of L-selection selectin;
  an increase in the level of MCP-1;
  an increase in the level of IL-1α;
  an increase in the level of IL-8; and
  an increase in the level of IFN-γ

The peripheral biological fluid, taken from mammal can be saliva, sweat, urine, serum or plasma. In certain embodiments, the peripheral biological fluid is serum or plasma.

Another aspect of the disclosure is a kit to be used to aid in the diagnosis of AD comprising individual probes for P-selectin and/or L-selectin. Optionally, the kit additionally incorporates one or more other known diagnostic biomarkers of AD.

A further aspect of the disclosure is a kit to be used in the prognosis or as an aid in the prognosis of AD comprising individual probes for one or more of L-selectin, MCP-1, IL-1α, IL-8 and IFN-γ. Optionally, the kit additionally incorporates one or more other known prognostic biomarkers of AD. Optionally, the diagnostic and prognostic kits are combined so as to incorporate all of the diagnostic and prognostic markers in one kit. The probe may be antibodies.

In a further aspect of the disclosure, the kit comprises a solid state device with probes attached to it. The solid state device may be a biochip.

The biomarkers disclosed herein can equally be taken together or with additional known biomarkers of AD such as tau protein or β-amyloid proteins, for screening of AD by taking biological fluids from patients not diagnosed or with a tentative diagnosis of AD and comparing the concentration of the biomarkers to a recognised control value of the biomarker in, for example, a healthy individual. The control value can be a measure of central tendency e.g. the mean or median value of a sample population described in a study in the literature. For example, Ponthieux et al. (2003) describe reference values for serum adhesion molecule concentrations in healthy individuals.

Also disclosed herein is the use of P-selectin and/or L-selectin in conjunction with one or more of MCP-1, IL-1α, IL-1β, IL-8, IFN-γ, MCP-1 and VEGF and/or other, known biomarkers of AD (e.g. β-amyloid proteins, tau protein in a test for AD, that may increase the diagnostic and prognostic power of the test by, for example, increasing its sensitivity (higher percentage of true positives i.e. testing positive for patients with AD) and/or specificity (high percentage of true negatives i.e. testing negative for patients without AD). It is desirable to achieve the target sensitivity and specificity with the minimum number of biomarkers.

When identifying the biomarkers of AD, it will be apparent to the person skilled in the art that as well as identifying the full length protein, the identification of a fragment (or several fragments) is possible, provided this allows accurate identification of the full length protein; for example, protease digestion of a protein followed by mass spectrometry of a small number of the resulting peptides, is routinely used to identify a protein. This method is often used to identify a spot on a protein gel. If the protein is an oligomer, identification of a single chain may be sufficient.

Subjects

Patients with a clinical diagnosis of AD (28 male and 44 female; mean age 75.6±7.2 years) and control subjects (2 male and 4 female; mean age 73.4±1.1 years) were enrolled from the Department of Neuroscience, Castellanza University, Milan.

Clinical diagnosis of probable AD was performed according to standard clinical procedures and followed criteria set by NINCDS/ADRDA (McKhann et al., 1984) and DSM-III-R (American Psychiatric Association, 1987). Briefly, diagnosis of probable AD was made by two independent physicians' evaluations and brain computerised tomography scans. Cognitive performances were measured by mini-mental state examination (MMSE) and the global deterioration scale (GDS). Longitudinal cognitive performances during a two year follow-up of patients with AD were assessed by MMSE scores (Doody et al., 2001). Patients with AD were divided into two groups according to MMSE scores; those with slow cognitive decline (AD losing <4.9 points/year) or those with fast cognitive decline (AD losing >5 points/year).

Patients and controls were Caucasians, and informed consent from each subject or AD patient was obtained. The study was approved by the Medical Ethical Committee of the Don Gnocchi Foundation, Milan.

Measurement of Analyte Plasma Levels (Italian Study)

The Evidence Investigator™ and Biochip Array Technology (Randox Laboratories, Crumlin, Northern Ireland, UK) were used for the simultaneous detection of multiple analytes from a single patient plasma sample. EDTA was used as anticoagulant for blood collection. The technology uses the Randox Biochip, a 9 mm² solid substrate supporting an array of discrete test regions with immobilized, antigen-specific antibodies. The arrays used were Cytokine Array I (analytes: EGF, IFN-γ, VEGF, IL-2, IL-4, IL-6, IL-8, IL-10, TGF-α, IL-1α, IL-1β and MCP-1, Catalogue Number EV3513) and Adhesion Molecules Array (analytes: E-selectin, L-selectin, P-selectin, ICAM-1 & VCAM-1, Catalogue Number EV 3519). Following antibody activation with assay buffer, standards and samples were added and incubated at 37° C. for 60 minutes, then placed in a thermo-shaker at 370 rpm for 60 minutes. Antibody conjugates (HRP) were added and incubated in the thermo-shaker at 370 rpm for 60 minutes. The chemiluminescent signals formed after the addition of luminol (1:1 ratio with conjugate) were detected and measured using digital imaging technology and compared with that from a calibration curve to calculate the concentration of the analytes in the samples.

Measurement of Analyte Plasma Levels (Austrian Study)

A second independent study, approved by the local ethics committee, was conducted in Austria using the Randox Adhesion Markers biochip on the Evidence Investigator™. Levels of adhesion proteins in the plasma of AD patients and healthy controls were compared (AD patients were initially categorized using MMSE and were verified as having AD using post-mortem examination; healthy patients were categorized using MMSE). A test for ACD and SCD was not implemented in this study. P-selectin levels in AD patients were found to be significantly reduced compared to controls (unpaired t-test P=0.044, FIG. 3). P-selectin mean levels in control and AD groups were 81.9 ng/ml (N=45; 12 males 33 females; average age 79.30 years) and 94.9 ng/ml (N=36; 8 males 28 females; average age 81.30 years), respectively.

Statistical Analysis

The data from the Italian study, both untransformed and transformed, were not normally distributed. Non-parametric Mann-Whitney and Kruskall-Wallis tests (using Dunn's paired comparisons test) were used for comparisons of AD and control and ACD, SCD and control, respectively. Data from the Austrian study was analysed using a t-test. Statistical significance was assumed at a level of p=<0.05.

Results

Plasma concentrations of IL-1α, IL-1β, IL-8, IFN-γ, MCP-1 and VEGF plasma levels were significantly greater in AD patients than in controls (Table 1). The concentrations of the adhesion molecules P-selectin and L-selectin were significantly lower than controls. Plasma concentrations of several analytes were found to differ between AD patients with SCD and AD patients with ACD (Table 2). Concentrations of the cytokines IL-1α, IL-8, IFN-γ and MCP-1 were all significantly greater in AD patients with SCD compared to AD patients with ACD or controls. The concentration of the adhesion molecule L-selectin was significantly lower in AD patients with ACD compared to AD patients with SCD or controls.

BIBLIOGRAPHY

1. Abdi et al (2006). J. AL Dis., 9: 293-348.
2. Akiyama et al. (2000). Neurobiol. Aging, 21: 382-421.
3. Chiapelli et al. (2006). Expert Rev. Neurother., 6: 1327-1336.
4. Dickson et al. (1988). Am. J. Pathol., 132: 86-101.
5. Doody R. S. et al. (2001). Arch. Neurol., 58: 449-454.
6. Hye et al. (2006). Brain, 129: 3042-3050.
7. Koutrobakis et al. (2004). Atherosclerosis, 176: 125-132.
8. Magro et al. (2004). 8. Dig. Dis. Sci., 49:1265-74.
9. Ponthieux et al. (2003). Clin. Chem., 49: 1544-1546.
10. Rebenko-Moll N. M. et al (2006). Curr. Opin. Immunol., 18: 683-689
11. Rogers et al. (1988). Neurobiol. Aging, 9: 939-349.
12. Small et al. (2000). Proc. Nat. Acad. Sci., 97(11): 6037-6042.
13. Zhang et al. (2004). Proteomics, 4: 244-256.

The invention claimed is:

1. An assay comprising the steps of:
    contacting a sample of a peripheral biological fluid obtained from a patient suffering from Alzheimer's disease with a probe capable of binding specifically to L-selectin, wherein the peripheral biological fluid is serum or plasma;
    measuring the concentration of L-selectin from the sample specifically bound to the probe; and
    providing the measured concentration of L-selectin specifically bound to the probe.

2. The assay of claim 1, wherein the probe capable of binding specifically to L-selectin is an antibody.

3. The assay of claim 2, wherein the antibody is a monoclonal antibody.

4. The assay of claim 2, wherein the antibody is a polyclonal antibody.

5. The assay of claim 1, further comprising the steps of:
    contacting the sample with a probe capable of binding specifically to a known biomarker of Alzheimer's disease;
    measuring the concentration of the known biomarker of Alzheimer's disease from the sample specifically bound to the probe; and
    providing the measured concentration of the known biomarker of Alzheimer's disease specifically bound to the probe.

6. The assay of claim 5, wherein the known biomarker of Alzheimer's disease is IL-1α.

7. The assay of claim 5, wherein the known biomarker of Alzheimer's disease is IL-1β.

8. The assay of claim 5, wherein the known biomarker of Alzheimer's disease is IL-8.

9. The assay of claim 5, wherein the known biomarker of Alzheimer's disease is IFN-γ.

10. The assay of claim 5, wherein the known biomarker of Alzheimer's disease is VEGF.

11. The assay of claim 1, wherein the peripheral biological fluid is serum.

12. The assay of claim 1, wherein the peripheral biological fluid is plasma.

13. The assay of claim 1, wherein the patient suffering from Alzheimer's disease has accelerated cognitive decline (ACD).

14. The assay of claim 1, wherein the patient suffering from Alzheimer's disease has slow cognitive decline (SCD).

* * * * *